(12) United States Patent
Sarkela et al.

(10) Patent No.: US 8,221,330 B2
(45) Date of Patent: Jul. 17, 2012

(54) MEASUREMENT FOR EEG REACTIVITY

(75) Inventors: Mika Sarkela, Espoo (FI); Juha Virtanen, Helsinki (FI); Hanna E. Viertio-Oja, Espoo (FI); Tapani Salmi, Vantaa (FI)

(73) Assignee: General Electric Company, Schenectady, NY (US)

(*) Notice: Subject to any disclaimer, the term of this patent is extended or adjusted under 35 U.S.C. 154(b) by 12 days.

(21) Appl. No.: 12/940,143

(22) Filed: Nov. 5, 2010

(65) Prior Publication Data

US 2011/0087127 A1     Apr. 14, 2011

Related U.S. Application Data

(62) Division of application No. 11/674,732, filed on Feb. 14, 2007, now Pat. No. 7,844,324.

(51) Int. Cl.
  *A61B 5/04* (2006.01)
(52) U.S. Cl. .................. 600/554; 600/544; 600/300
(58) Field of Classification Search .......... 600/544–546, 600/552–559
See application file for complete search history.

(56) References Cited

U.S. PATENT DOCUMENTS

| | | | |
|---|---|---|---|
| 4,201,224 A | 5/1980 | John | |
| 4,214,591 A | 7/1980 | Sato et al. | |
| 5,230,344 A | 7/1993 | Ozdamar et al. | |
| 5,788,648 A | 8/1998 | Nadel | |
| 6,256,531 B1 | 7/2001 | Ilmoniemi et al. | |
| 6,416,480 B1 | 7/2002 | Nenov | |
| 2003/0073921 A1 | 4/2003 | Sohmer et al. | |

OTHER PUBLICATIONS

EEG Reactivity in the Prognosis of Severe Head Injury, Eva Gutling M.D. et al., Neurology 45, May 1995, pp. 915-918.
Feature Extraction from the Electroencephalogram by Adaptive Segmentation, Gunter Bodenstein et al., Proceedings of the IEEE, vol. 65, No. 5, May 1977, pp. 64-652.
Automatic EEG Analysis: A Segmentation procedure Based on the Autocorrelation Function, D. Michael et al., Electroencephalography and Clinical Neurophysiology, 1979, 46: 232-235.
Automatic Detection and Localization of Epileptic Foci, F. H. Lopes Da Silva et al., Electroencephalography and Clinical Neurophysiology, 1977, 43: 1-13.

*Primary Examiner* — Charles A Marmor, II
*Assistant Examiner* — Carrie R Dorna
(74) *Attorney, Agent, or Firm* — Andrus, Sceales, Starke & Sawall, LLP (57) ABSTRACT

The invention relates to a method and apparatus for assessing the reactivity observable in a certain physiological signal, especially the EEG signal, of a comatose subject. In order to obtain an objective and a reliable measure of the reactivity automatically and without the presence of a trained EEG specialist, a valid signal model is constructed for an EEG signal obtained from the subject. A time reference corresponding to a stimulus is applied and further signal data is obtained from the time series, the further signal data being subsequent to the time reference. By employing the further signal data, the method tests whether the signal model remains to be a valid signal model for the EEG signal also after the stimulus, and indicates, based on the test, whether reactivity is present in the physiological signal.

13 Claims, 8 Drawing Sheets

MEASUREMENT FOR EEG REACTIVITY

CROSS REFERENCE TO RELATED APPLICATION

This application is a divisional application of prior U.S. patent application Ser. No. 11/674,732, filed on Feb. 14, 2007, now issued as U.S. Pat. No. 7,844,324, entitled MEASUREMENT FOR EEG REACTIVITY

FIELD OF THE INVENTION

The present invention relates to the assessment of the reactivity of the central nervous system of a patient to external stimulation as observable on/in a physiological signal, especially an EEG signal. Below, the reactivity observable on/in a physiological signal is termed physiological signal reactivity. If the physiological signal concerned is an EEG signal, the said reactivity is termed briefly EEG reactivity.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

Different derangements of internal system homeostasis disturb the environment in which the brain operates, and therefore the function of the brain and the resulting EEG are disturbed. The EEG signal is a very sensitive measure of the neuronal derangements, which may reflect in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

Generally, if a patient is unconscious (without sedation), the reason in 30 to 40 percent of the cases is intracranial, whereas in 60 to 70 percent of the cases unconsciousness is due to hypoxic-ischaemic, metabolic, or toxic reasons. This kind of general unconsciousness is currently monitored with the help of the Glasgow Coma Scale (GCS). It defines the patient (un)consciousness by using three parameters: the best eye opening response, the best motoric response, and best response to speech. The final score represents the sum of the scores of the three categories. Table 1 below illustrates the Glasgow Coma Scale. Although the Glasgow Coma Scale is subjective and inter-rater variability may exist, it is the most widely used scoring system to assess patients with traumatic brain injury, for example.

TABLE 1

The Glasgow Coma Scale

| Criterion | | Points |
|---|---|---|
| Eye Opening Response | Spontaneous | 4 |
| | Opens to verbal command | 3 |
| | Opens to pain | 2 |
| | None | 1 |
| Verbal response | Oriented | 5 |
| | Confused | 4 |
| | Inappropriate words | 3 |
| | Incomprehensible sounds | 2 |
| | None | 1 |
| Motor response | Obeys commands | 6 |
| | Localises pain | 5 |
| | Withdraws from pain | 4 |
| | Abnormal flexion | 3 |
| | Extends to pain | 2 |
| | None | 1 |
| Total | | 3-15 |

Diagnostically, the EEG is only rarely specific, since many systemic disorders of the brain produce similar EEG manifestations. However, an EEG signal may be of critical value, as it may differentiate between broad categories of psychogenic, epileptic, metabolic-toxic, encephalitic, and focal conditions, for example.

In a healthy sleeping subject, the EEG is reactive to various stimuli according to the sleep stages. For a comatose patient, a test of the reactivity of the EEG signal to external stimulation is an important assessment tool for a clinician, since it provides significant information regarding the state and outcome of the patient. EEG reactivity may reveal potentially treatable conditions and also provide information of the level of drug-induced sedation. While some conclusions about the probability of a recovery can be drawn from the raw EEG signal as such, it has been shown that reactivity of the EEG signal to stimulation, i.e. a detectable change in the EEG signal after a stimulus as compared to the pre-stimulus situation, is a more specific indicator of a favourable outcome, cf. E. Gütling et al.: *EEG reactivity in the prognosis of severe head injury*, Neurology 1995; 45:915-918. Therefore, testing the EEG reactivity is an essential part of the EEG examination of a comatose patient. Moreover, the test of EEG reactivity provides information regarding the state of a patient for whom the GCS or another observational scoring system is not applicable. This is the case, for example, when neuromuscular blocking agents have been administered to the patient, which makes the patient unable to respond and thus the observational scoring systems inapplicable.

At present, the EEG reactivity is assessed by an EEG specialist trained to interpret EEG waveforms. In practice, ICU (Intense Care Unit) doctors or nurses, who are skilled in making GCS-type assessments, are usually not capable of interpreting the EEG waveforms, and therefore a consulting EEG specialist has to be called in for the test of EEG reactivity. Various types of stimuli, such as auditory (shouting the patient's name, blowing a horn), painful (nasal tickle), and somatosensory (passive eye opening, pinching the skin, squeezing nail beds, shaking) stimuli, may be applied in the test. The EEG specialist annotates the time instant of the stimulation and compares the recorded EEG signal before and after the annotated time instant. Often the EEG signal shows reactivity only to some of the given stimuli; in this case reactivity is considered to be present.

The test of the EEG reactivity is thus currently based on the visual assessment of the EEG waveform prior to and after the stimulation, since developing an automated testing procedure is complicated. This is mainly due to the high inter-patient variability, which may cause great variations between different patients both in the initial EEG signal waveforms and in the reactions to stimuli. The initial EEG signal waveforms, for example, may vary greatly depending on the state of the patient. The reactions that may be seen in the EEG signal after the stimulation comprise different types of responses, such as slow wave responses, voltage reduction and filtering of remnants of the basic rhythm, and flattening of voltage without or with blocking of slow waves, cf. Gütling et al.: *EEG reactivity in the prognosis of severe head injury*, Neurology, 1995; 45:915-918. The visual assessment of the EEG is performed by a specialist, since he/she must understand the features of the EEG and take into account various patient-specific factors, such as the age, the level of drowsiness, and the metabolic state of the patient, as well as the possible disorders and their effect on the basic EEG signal.

Due to the above-described high variability between different patients, no automatic quantification tools exist for assessing the EEG reactivity, but a specialist is needed for the interpretation of the EEG waveforms. Consequently, the assessments are subjective and dependent on the level of expertise of the specialist. One possible source of the inter-individual variation in the EEG reactivity is the status of peripheral/sensory nervous system, which affects the transmission of the stimulus to the brain. The state of the sensory pathways may be affected by either medication or possible injury due to trauma or disease.

The present invention seeks to alleviate or eliminate the above-mentioned drawback and to devise an automated mechanism for evaluating EEG reactivity.

SUMMARY OF THE INVENTION

The present invention seeks to provide an automated reactivity test that provides an objective and a reliable measure of physiological reactivity, especially EEG reactivity. The invention further seeks to obtain an automated EEG reactivity test, sensitive even to the shortest responses of the cortex, which may occur in comatose patients, for example.

In the present invention, a signal model is constructed for the EEG signal from the EEG signal data obtained from a subject. The signal model here refers to a formula that describes signal characteristics and thereby enables subsequent testing whether a stimulus causes a change in the stationarity of the signal, i.e. occurrence of non-stationarity in the signal. The change in the stationarity may be a quick, transient-type reversible change or a long-time or rather permanent change in the stationarity. The signal model may be, for example, a formula that enables the prediction of a signal value based on previous signal values. Prediction error, which is the difference between the predicted signal value and the measured signal value, may be used to test if signal stationarity has changed. This kind of signal prediction is typically done with autoregressive (AR) modeling. In autoregressive modeling, AR parameters are derived, which characterize the signal spectral properties. The AR parameters may be derived, for example, by solving so-called Yule-Walker equations, which include a p×p autocorrelation matrix, where p is equal to model order. However, as is discussed below, an autocorrelation function itself may also serve as a signal model, since it characterizes the spectrum of the signal. Comparison of autocorrelation function values calculated prior to and after the stimulus therefore allows a quick method for testing whether the stimulus caused a change in the stationarity of the signal. Alternatively, a change in the AR parameters may be used to detect a change in signal stationarity. Other formulas that may be used to produce signal model include Hjort descriptors, Teager energy operator (TEO), nonlinear energy operator (NLEO), and signal derivatives, for example. All the above-mentioned formulas may be sequentially applied to a time series signal and they characterize the spectral content and/or the variance (power) of the signal.

The signal model is preferably constructed for each stimulus to be given to stimulate the subject, thereby to ensure that the signal model represents current signal characteristics. In response to the stimulus, the validity of the signal model is tested to see if the constructed model remains as a valid model for the signal data in a certain time window after the stimulus.

If the constructed model is not a valid signal model for the time series comprising signal samples subsequent to the stimulus, it indicates that the stimulus caused a change in the stationarity of the signal. Thus, if this occurs, it is decided that reactivity is present in the signal. However, if the signal model remains as a valid signal model over the said time window, there is no substantial change in the stationarity of the signal during that time window and thus it is decided that reactivity is not present in the The reactivity of the central nervous system of the subject may also be determined with respect to another physiological signal than the EEG, such as the ECG.

Thus one aspect of the invention is providing a method for assessing the physiological signal reactivity of a subject. The method includes constructing, based on a time series of a physiological signal obtained from a subject, a signal model for the physiological signal, applying a time reference corresponding to a stimulus, and obtaining further signal data from the time series, the further signal data being subsequent to the time reference. The method further includes testing whether the signal model is a valid signal model for the physiological signal, wherein the testing includes employing the further signal data and indicating, based on the testing, whether reactivity is present in the physiological signal.

Another aspect of the invention is that of providing an apparatus for assessing the physiological signal reactivity of a subject. The apparatus includes a calculation unit configured to construct, based on a time series of a physiological signal obtained from a subject, a signal model for the physiological signal, a control unit configured to apply a time reference corresponding to a stimulus, and a reception unit configured to receive further signal data from the time series, the further signal data being subsequent to the time reference. The apparatus further comprises a test unit configured to test, through employment of the further signal data, whether the signal model is a valid signal model for the physiological signal and an indicator unit, responsive to the test unit, configured to indicate, whether reactivity is present in the physiological signal.

The invention enables an objective and a reliable measure of the EEG reactivity to be obtained without the presence of an EEG specialist, which enhances patient monitoring in an ICU environment. Furthermore, the invention enables exact detection and temporal positioning of the reactivity events in the signal. For example, the delay from the stimulus to the onset of reactivity may be measured.

A further aspect of the invention is that of providing a computer program product by means of which known patient monitoring devices may be upgraded and thus their applicability extended to include the assessment of physiological signal reactivity. The program product includes a first program code portion configured to construct, based on a time series of a physiological signal obtained from a subject, a valid signal model for the physiological signal and a second program code portion configured to apply a time reference corresponding to a stimulus. The program product further comprises a third program code portion configured to test, through employment of further signal data of the time series, whether the signal model is a valid signal model for the physiological signal, wherein the further signal data is subsequent to the time reference and a fourth program code portion, responsive to the third program code portion, configured to indicate whether reactivity is present in the physiological signal.

In one embodiment of the invention, the measurement employs transcranial magnetic stimulation (TMS) of the subject's cortex. Since the stimulus is in this case not sensed through the sensory nervous system, the state of the neural pathways does not affect the measurement, but the measurement is specific to the cortical state of the subject. Furthermore, TMS offers an opportunity to activate relatively large populations of cortical neurons, hence supplying in a way much stronger stimulation to the cortex than what would be possible through sensory stimulation. In this way, TMS provides an efficient tool for assessing different levels of deep sedation or unconsciousness.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIGS. 1 to 9 in the appended drawings, wherein:

FIG. 8b illustrates the operational units of the control unit of FIG. 8a; and

DETAILED DESCRIPTION OF THE INVENTION

As discussed above, the present invention rests on adaptive segmentation of the physiological signal for detecting changes in the stationarity of the signal. In adaptive segmentation, the signal is not processed in fixed length time windows termed epochs, as is common in EEG analysis, but rather on a sample-by-sample basis.

Figure 1:
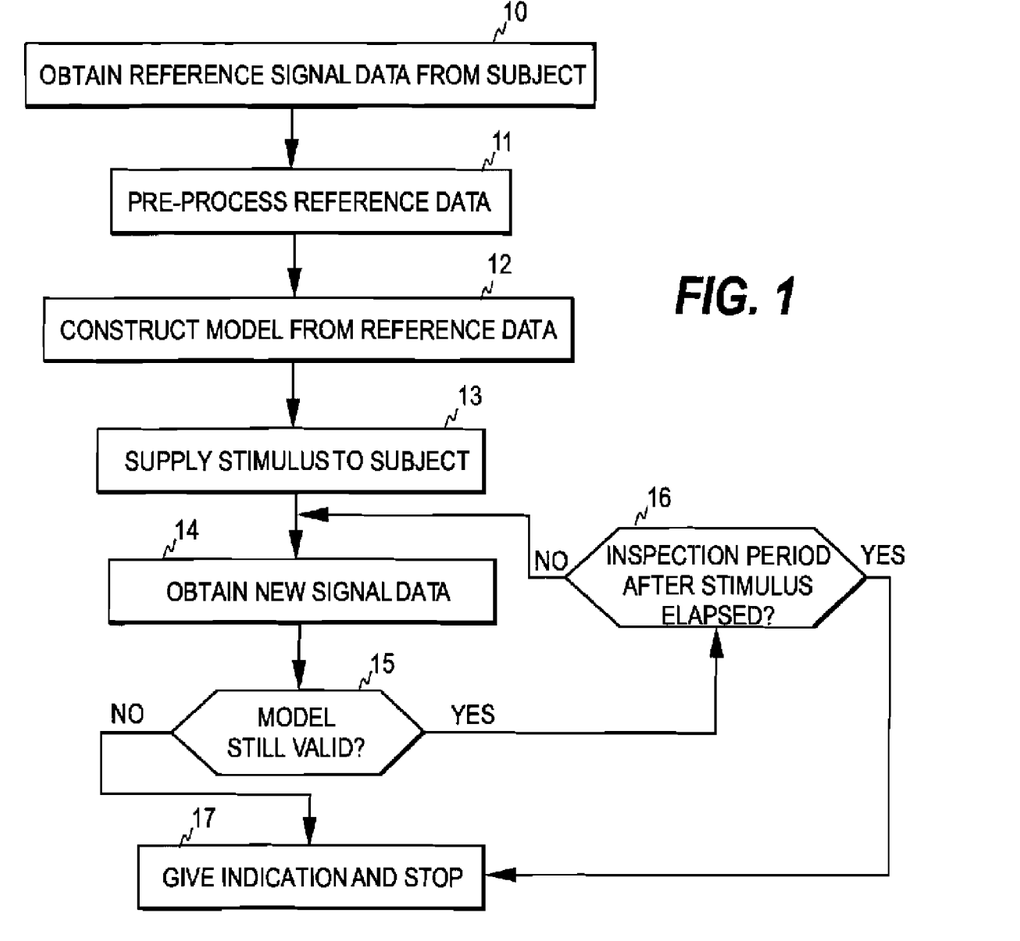
FIG. 1 is a flow diagram illustrating one embodiment of the method of the invention.

FIG. 1 illustrates one embodiment of the present invention. An EEG signal measured from a patient (step 10) is first digitized to obtain a time series of EEG signal data. The sampled EEG signal may then be filtered to exclude high- and low-frequency artifacts (step 11). The signal data obtained initially from the patient may also be termed reference signal data in this context, since it is employed at step 12 to construct a valid signal model for the current time series. The signal model constructed enables prediction of signal values for the time series and a valid signal model meets predetermined criteria in the prediction. For example, the signal model may be regarded as a valid model as long as the prediction error remains below a certain threshold value.

A stimulus may then be given at step 13. The stimulus signal may assume any suitable form and may thus be an electrical, a mechanical, an electromagnetic, or an auditory stimulus, for example. Moreover, the stimulus is preferably predetermined in the sense that the system knows the parameters defining the stimulus. A time label indicating the time instant of the stimulus is attached to the EEG signal data to indicate the moment of the stimulus in the data sequence. As also discussed below, in one embodiment of the invention the stimulus is not supplied through the sensory nervous system of the subject, thereby to prevent the actual cortical state of the subject from being obscured by abnormally functioning neural pathways.

EEG signal data subsequent to the stimulus is then obtained from the time series at step 14 and the obtained data is utilized to test whether the signal model remains as a valid model for the signal also after the stimulus, step 15. If the test indicates that the model is not any more valid, it is decided that reactivity is present and the user is informed of the presence of reactivity (step 17). Various decision rules may be employed to decide when the model turns into an invalid model. For example, the model may have to be an invalid model continuously for a certain period, before it is regarded as an invalid model.

If the constructed signal model remains as a valid signal model for a certain inspection period, such as 30 seconds, after the stimulus, the process decides that no reactivity is present and quits the testing. The user is informed that no reactivity was found (steps 14 to 17).

FIG. 1 illustrates the method for one stimulus signal. If a new stimulus is given, the above steps may be repeated, i.e. the signal model is constructed before each stimulus to ensure that the model corresponds to the current EEG of the patient. Furthermore, if the stimulus signal is not supplied immediately after the signal model is available, the validity of the model may be tested already prior to the stimulus to ascertain that the model remains as a valid model until the time instant of the stimulus.

Figure 2:
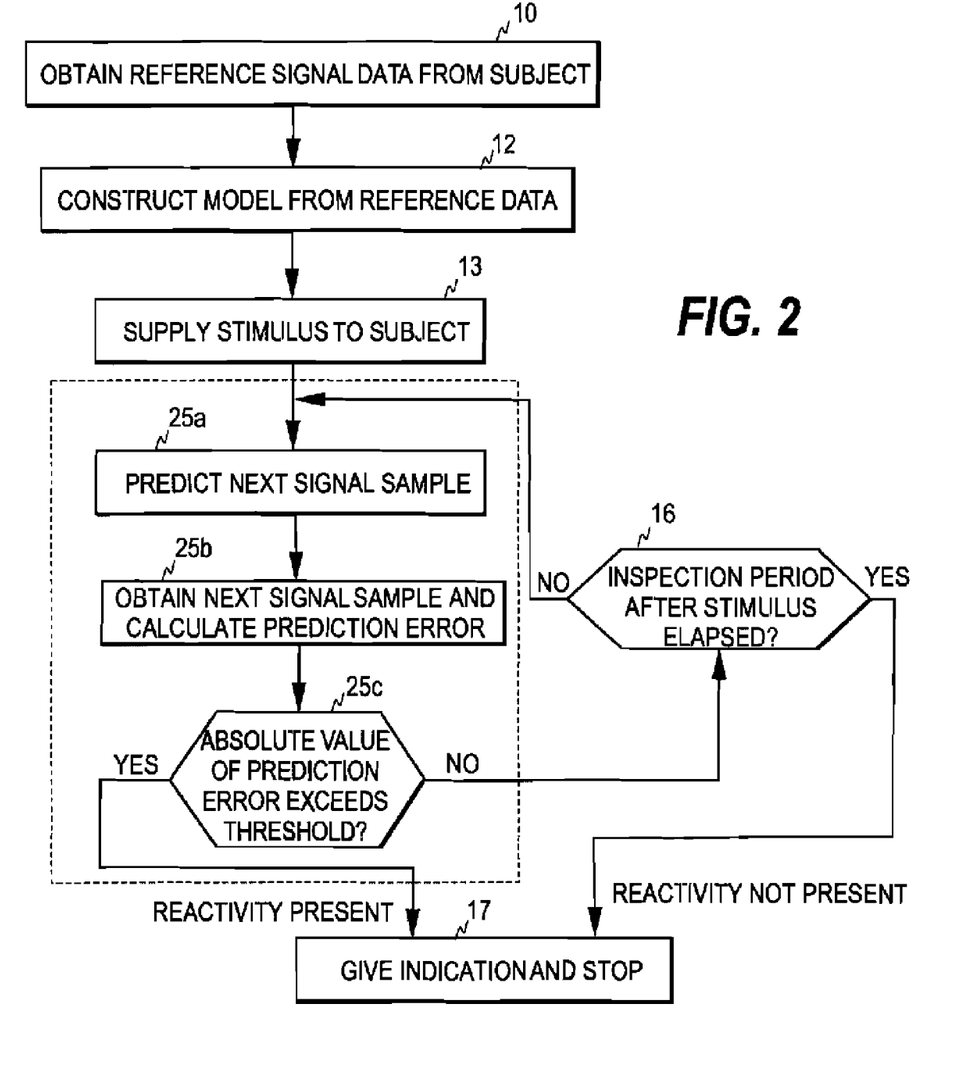
FIG. 2 is a flow diagram illustrating another embodiment of the method of the invention.

FIG. 2 illustrates an embodiment of the invention, in which the testing of the validity of the signal model is carried out by calculating a prediction error. The validity of the model is now tested in the steps shown within the dashed square. Each of the remaining steps corresponds to one of the steps in FIG. 1; corresponding steps are designated with the same reference numbers as in FIG. 1. Step 11 of FIG. 1 is omitted in FIG. 2, since artifact rejection is optional.

In the embodiment of FIG. 2, the value of the next signal sample is predicted at step 25a based on the model constructed at step 12. Based on the actual and predicted values of the next signal sample, the process defines a prediction error, which may simply be the difference of the two values (step 25b). At step 25c, the system then compares the absolute value of the prediction error with a certain threshold value. In other words, the signal model is regarded as a valid model as long as the absolute value of the prediction error remains below the threshold value.

The signal model and the evaluation of its validity after the stimulus may be carried out similarly as in adaptive signal segmentation techniques used for analyzing the fine structure of an EEG. In adaptive signal segmentation the signal is sequentially processed in relatively short epochs, for example, sample-by-sample basis. If a change in the stationarity of the signal is detected, a segment boundary is inserted. The technique may be applied in the present invention by processing the new data samples obtained after the stimulus on a sample-by-sample basis to detect a possible change in the stationarity of the signal.

In one embodiment of the invention, the determination of the signal model and its validity may be based on an AR model and a prediction error, as described by [F. H. Lopes da Silva et al.: *Automatic Detection and Localization of Epileptic Foci*, Electroencephalography and Clinical Neurophysiology, 1977; 43:1-13]. In this method, reference EEG is modeled by an AR model and the next EEG sample $\hat{s}(n)$ is predicted by filtering the EEG signal $s(n-p), \ldots, s(n-2), s(n-1)$ with an inverse AR filter, based on the model. The predicted values are given by the equation:

$$\hat{s}(n) = -\sum_{i=1}^{p} a(i)s(n-i),$$

where $\alpha$ are the coefficients of the AR filter. The difference between the predicted value $\hat{s}(n)$ and the actual signal value $s(n)$ is called the prediction error $\epsilon(n)$:

$$\varepsilon(n) = s(n) - \hat{s}(n) = s(n) + \sum_{i=1}^{p} a(i)s(n-i) = \sum_{i=0}^{p} a(i)s(n-i),$$

where $\alpha(0)=1$ by definition. Based on the assumption that EEG is normally distributed white noise also the prediction error $\epsilon(n)$ should be normally distributed white noise. When a change in the EEG stationary occurs, $\epsilon(n)$ thus differs from normal distribution. The squared ratio of the prediction error $\epsilon(n)$ to its standard deviation is integrated within a short time window WL, such as 0.25 s. The resulting formula is used as a decision function $D_1$, which is compared with a threshold value to detect when a change occurs in the stationarity of the signal. The decision function $D_1$ may be obtained as follows:

$$D_1(n) = \sum_{n=k-WL+1}^{k} \left[\frac{\varepsilon(n)}{\sigma_\varepsilon}\right]^2$$

where $\sigma_\epsilon$ refers to the standard deviation of the prediction error.

Figure 3A:
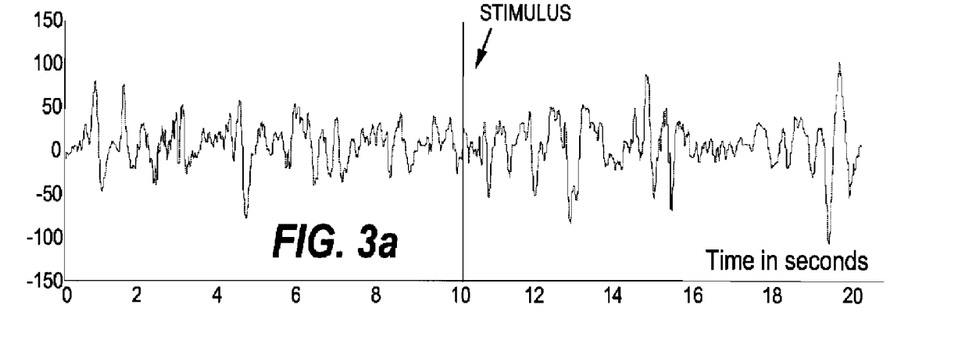
FIGS. 3a and 3b illustrate the performance of one embodiment of the invention.
Figure 3B:
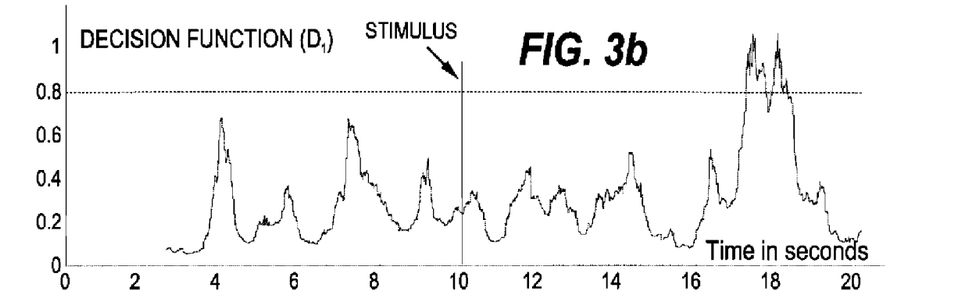

FIGS. 3a and 3b illustrate the performance of a method in which the determination of the signal model is based on the above-described autoregressive model. FIG. 3a shows a 20 second segment of an EEG signal measured from a patient. The stimulus is applied approximately in the middle of the segment. In this example, EEG reactivity can be seen as the attenuation of the signal, which is one form of EEG reactivity. The attenuation starts at about time instant t=16 seconds.

FIG. 3b illustrates the value of the decision function $D_1$ calculated in the above-described manner. The first 1.5 seconds of the signal are employed to construct the AR model and the threshold value for the decision function is 0.8 in this example. The pseudo code for the detection procedure is described below:

```
if D(n) ≧ threshold ,
    reactivity detected,
    break,
else
    n = n + 1
    continue,
end
```

As can be seen from FIG. 3b, the decision function first remains below the threshold but reaches the threshold substantially at the same time as the attenuation of the EEG starts.

An other commonly used adaptive segmentation method is the Spectral Error Measure (SEM). Spectral error may be estimated based on the difference of the autocorrelation functions of two windows, as first proposed by [D. Michael and J. Houchin: Automatic EEG Analysis: *A Segmentation Procedure Based on the Autocorrelation Function*, Electroencephalography and Clinical Neurophysiology, 1979; 46:232-235]. In this embodiment of the invention, a first autocorrelation function derived from a time window that precedes the stimulus thus represents reference data. The reference data is compared with a second autocorrelation function derived from a second time window belonging to the inspection period. The second time window may be widened as new data samples are obtained after the stimulus or the second time window may correspond to a fixed-size moving window, which slides over the signal segment that corresponds to the inspection period.

Figure 4A:
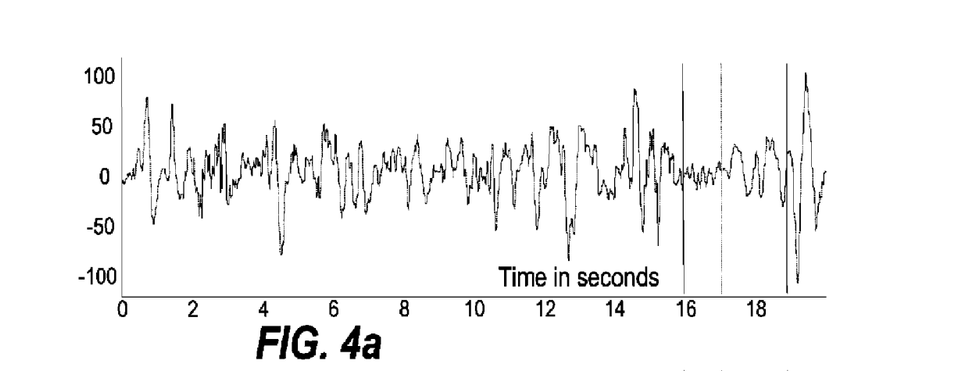
FIGS. 4a and 4b illustrate the performance of another embodiment of the invention.
Figure 4B:
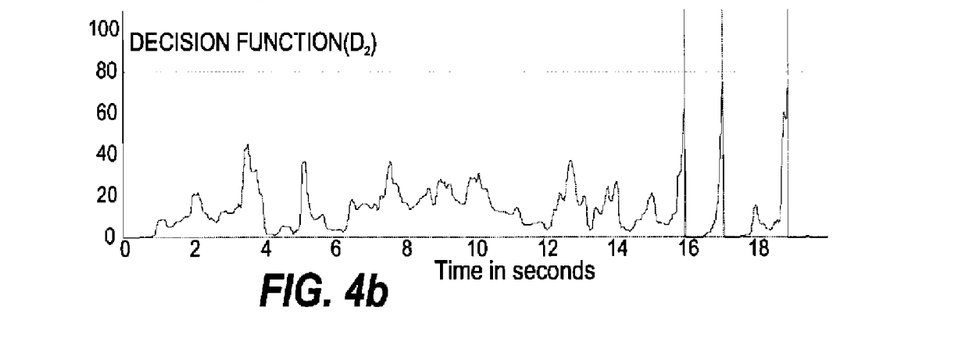

FIGS. 4a and 4b illustrate the performance of a method in which the SEM method is used to detect EEG reactivity. FIG. 4a again shows a 20 second segment of the EEG signal. As in FIG. 3a, the stimulus is applied approximately in the middle of the segment. In the example of FIGS. 4a and 4b, the decision function $D_2$ is the squared difference of two autocorrelation functions derived from short time windows (e.g. 0.25 s) and divided by the product of autocorrelation functions at zero lags. The decision function is given by the equation:

$$D_2(n) = \frac{\sum_{k=-\infty}^{\infty} (r_x(k,n) - r_x(k,0))^2}{r_x(0,n)r_x(0,0)}$$

where $r_x(k,n)$ is the autocorrelation function of the second time window, $r_x(k,0)$ is the autocorrelation function of the first time window, $r_x(0,n)$ is the autocorrelation function of the second time window at zero lag and $r_x(0,0)$ is the autocorrelation function of the first time window at zero lag.

The above formula is closely related to the formula used in the above-mentioned article by D. Michael and J. Houchin. Segment boundaries denoted with vertical lines in the figures represent changes in the stationarity of the signal. A change in the stationarity in turn represents EEG reactivity. In the simplest form of the detection, only one boundary is required to detect EEG reactivity. However, in this example EEG reactivity is manifested as an attenuation of short duration and therefore both the start and the end of the attenuated EEG segment are detected. In this example, segment boundaries are inserted temporally in the position, where the threshold value is reached. A segment boundary may also be inserted to the position where the decision function starts to increase before it reaches the threshold value. This can be done with a specific backtracking procedure, for example with the so-called Page-Hinkley test.

Alternatively, spectral error measure may be estimated from the prediction error time series, as proposed by G. Bodenstein and H. M. Praetorius, *Feature Extraction from the Electroencephalogram by Adaptive Segmentation*, Proceedings of the IEEE, 65;(5): 642-652, 1977. Furthermore, instead of an autocorrelation function, another function or quantity that characterizes the spectral content and/or the variance (power) of the signal may be employed to form the decision function.

In the examples of FIGS. 3 and 4, the validity of the signal model is tested already before the stimulus. However, the model becomes invalid only clearly after the stimulus, i.e. around t=16 seconds when the attenuation in the EEG starts.

Figure 5A:
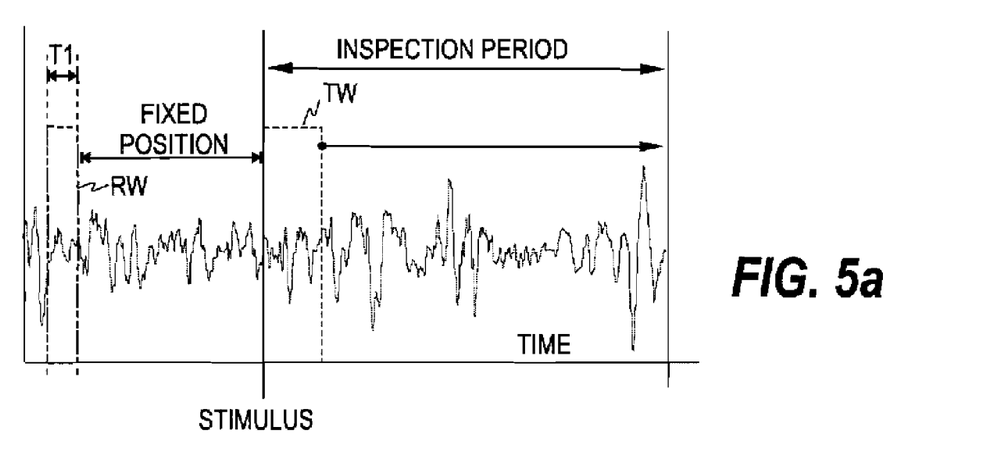
FIGS. 5a to 5c illustrate various mechanisms for obtaining reference data for the calculation of the signal model.
Figure 5B:
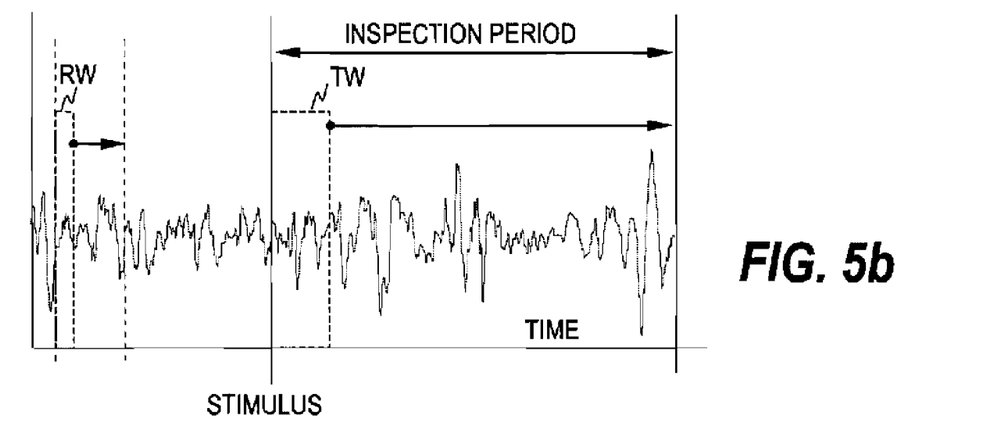
Figure 5C:
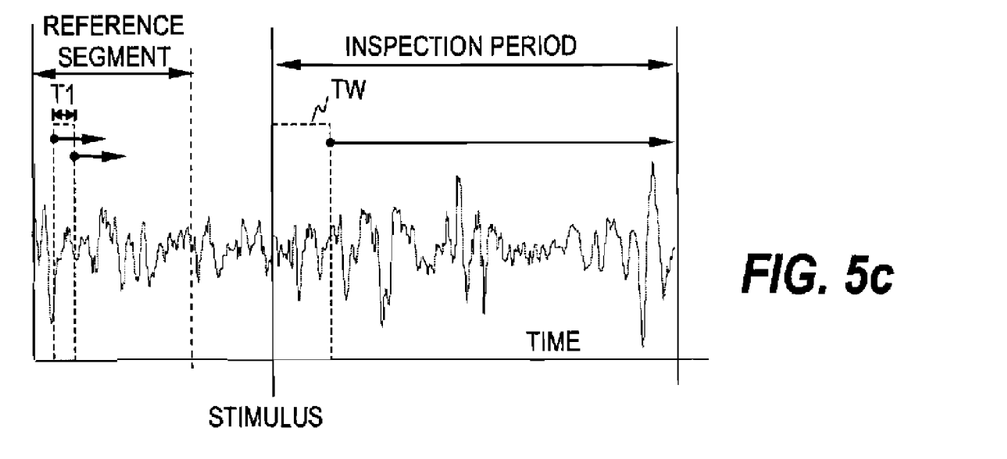

Although the above examples use simple Euclidean distance based error measures, the error measure may also be based on a statistic quantity, such as Kullback divergence or generalized likelihood ratio. Although the above examples use only one or two time windows, like a reference window for calculating the signal model and a test window for testing the occurrence of reactivity, the method may employ more windows and additionally use the union of two or more windows in the decision function. As is shown in FIG. 5a, the reference window RW is typically fixed in its temporal position relative to the stimulus and not widening. However, the reference window may also widen, although the first signal sample of the reference window may be fixed. This is illustrated in FIG. 5b. Alternatively, the reference window may be fixed in its size, but sliding through a certain reference segment of the time series, as is shown in FIG. 5c. In one alternative, the reference and test windows may be jointed together and may be moving or widening. The test window may also be part of a larger reference window. The reference window may also be, partly or entirely, after the stimulus if the patient response is slow and the windows used are short.

Although an AR model is used for signal prediction in the above examples, other methods like Kalman filtering, radial basis functions, or neural networks may also be utilized. Instead of a single channel signal, multiple EEG channels may also be analyzed simultaneously. Multi-channel EEG signal data may also be utilized in the decision function, for example by replacing the single-channel autocorrelation function with a multi-channel cross-correlation function.

Instead of calculating a prediction error based on the model and the actual signal value, the testing of the validity of the original model may also be carried out by constructing a new model based on the latest signal data and comparing the new model with the original model. If a significant change is detected between the models, reactivity is detected.

The stimulus applied may assume various forms. Furthermore, the time instant of the stimulus may be aligned with the EEG signal in a plurality of ways:

1. The monitoring device may generate the stimulus, such as a TOF (Train of Four) electric stimulus. The monitoring device attaches one or more time labels to the EEG signal data, which indicate the time instant of the stimulus signal.
2. The user may give the stimulus and indicate the corresponding moment to the monitoring device. The user may, for example, push a button when giving the stimulus. The monitoring device attaches a time label to the EEG signal data, which corresponds to the time instant indicated by the user.
3. The monitoring device may detect the stimulus given by the user. For example, the user may generate a particular audio signal, which the monitoring device detects. The monitoring device attaches one or more time labels to the EEG signal data, which indicate the time instant of the stimulus signal detected.
4. The monitoring device may prompt the user to give a particular stimulus. The temporal alignment of the EEG and stimuli may be carried out in one of the above ways.

If the monitoring device generates the stimulus, it may assess the EEG reactivity repeatedly by applying at least one stimulus at regular intervals, e.g. every 30 minutes. In this way, the EEG reactivity may be monitored continually. The monitoring device may then keep track of the trend of the EEG reactivity and display it graphically.

Figure 6:
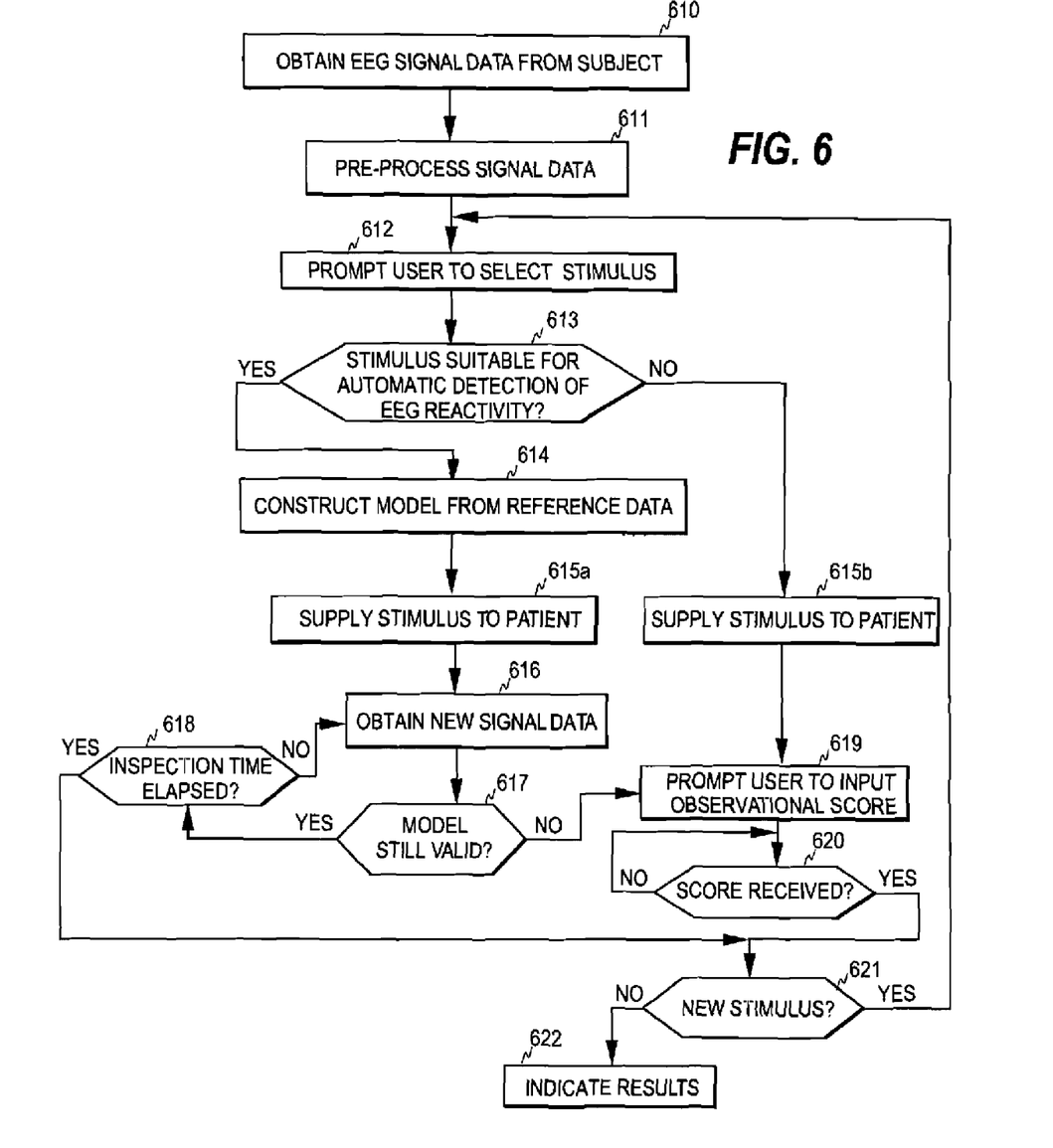
FIG. 6 illustrates an embodiment of the invention in which automatic detection of EEG reactivity is combined with a GCS-type scoring system.

In a further embodiment of the invention, which is illustrated in FIG. 6, automatic detection of EEG reactivity is combined with a GCS-type scoring system, which the user may perform with the assistance of the monitoring device of the invention. The said scoring system may be any other observational scoring system in which the user, such as an ICU doctor or nurse, examines the external responses of the patient. In this example, the observational scoring system utilizes the following four types of stimuli: a vocal stimulus, a noisy stimulus, a TOF stimulus, and a tetanic stimulus. The stimuli are used in the above-mentioned ascending order of intensity and if no observable response is obtained to a certain stimulus, the process proceeds to use the next stimulus.

In this embodiment, the first steps 610 and 611 correspond to steps 10 and 11 of the embodiment of FIG. 1. As the observational scoring system involves the use of four types of stimuli in ascending order of intensity, the user first selects the least intense stimulus signal, which is in this example a standardized "open your eyes" command supplied from a sound record. Since the order of the stimuli is fixed, the apparatus may also pre-select the stimuli and prompt for user confirmation on the selection made (step 612).

The monitoring device may check whether the stimulus signal given is such that the EEG reactivity is to be detected automatically based on it (step 613). All stimulus signals selected by the user are not necessary suitable for automatic detection of EEG reactivity and the user may also be given the chance to select whether assistance is to be provided by the device. Therefore, the monitoring device constructs the signal model only if the stimulus given is suitable for automatic detection of EEG reactivity, or if the user wishes the device to provide assistance. If the stimulus is not suitable for automatic detection of EEG reactivity or if the user does not wish the device to evaluate whether reactivity is present, the stimulus is supplied and the user is prompted to assess the resulting reactivity (steps 615b and 619).

If automatic detection of EEG reactivity is required, the monitoring device constructs the signal model (step 614), supplies the stimulus (step 615a), and tests the validity of the signal model after the stimulus (steps 616-618). If it is detected at step 617 that the signal model cannot any more predict the signal accurately, the user is prompted to input the score for the observational scoring system (step 619). Upon receiving the score from the user, the monitoring device prompts whether the user wishes to continue and to give a new stimulus (step 621). If so, the process jumps back to step 612 and the user is prompted to select or confirm the next stimulus. In this example, the next stimulus is a noisy stimulus consisting of standardized noise bursts, which may be supplied to the patient with headphones.

When the user has finished scoring the subject, he/she indicates that no more stimuli are needed (step 621/no). After this, the monitoring device determines the total score of the observational scoring system (step 622). In the above manner, the user may be prompted to input the score for the observational scoring system only if the process detects that reactivity is present in the EEG. Furthermore, as is discussed below, the method of the invention may be expanded to a system in which the reactivity is quantified.

Instead of a standardized scoring system any subset or modified set of stimuli may be used. The apparatus/system of the invention may be configured to give the user a possibility to pre-configure a particular set of stimuli that are prompted in a predetermined order. It is advantageous that a stimulus of lower intensity precedes a stimulus of higher intensity so that if a response is observed at a particular level of intensity the process may be stopped to avoid unnecessary interference of the patient. Pre-configured stimuli sequences, which the said sets may form, may also be utilized so that the apparatus/system of the invention starts with the least intense stimulus and automatically proceeds to the next stimulus of the sequence, if no response is detected to the stimulus just given. In this embodiment, the apparatus thus determines the need of a further stimulus and then gives the said stimulus without user input if the need exists.

Figure 7:
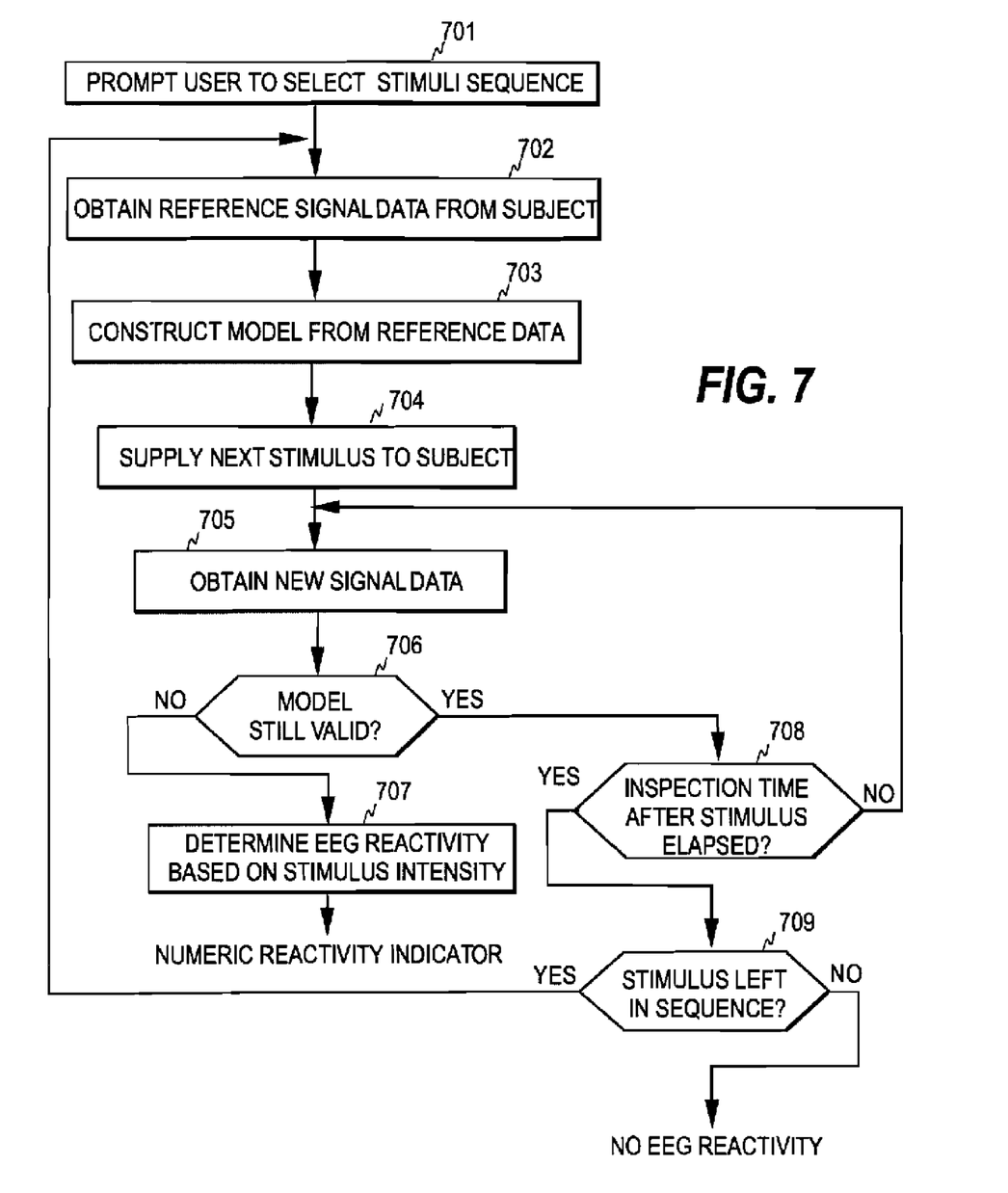
FIG. 7 illustrates an embodiment of the invention for quantifying the reactivity.

In a further embodiment of the invention, which is illustrated in FIG. 7, a numeric value for the EEG reactivity may be obtained automatically even though the presence/absence of EEG reactivity is still determined similarly, i.e. in an on/off-manner. This is accomplished so that the intensity of the stimulus determines the numeric value of the EEG reactivity: the less intensive the stimulus required to produce reactivity detection, the higher the value of EEG reactivity, and vice versa. When combined with the above-mentioned pre-configured stimuli sequences, this embodiment may be used to automatically produce a score similar to that of the commonly used observational scoring systems, such as the GCS or the Ramsay scoring system. In the embodiment of FIG. 7, the user thus first selects one of the pre-configured stimuli sequences (step 701) and the apparatus first supplies the least intensive stimulus of the sequence selected (step 704), after having constructed the signal model based on EEG reference data acquired from the subject (steps 702 and 703). After the stimulus, the validity of the signal model is tested in the above-described manner (steps 705, 706, and 708) for the segment corresponding to the inspection period. If no reactivity is detected within the said segment and if there is still at least one stimulus available in the sequence, the apparatus returns back to step 702 to give the next stimulus in the sequence (step 709).

If it is detected at step 706 that reactivity is present, the apparatus determines the numeric value of the reactivity based on the intensity of the latest stimulus given (step 707). If reactivity is not detected after any of the stimuli in the sequence, it is decided that no EEG reactivity is present (step 709/no).

In one embodiment of the invention, a numeric value of the reactivity may be obtained based on the magnitude of the decision function; the greater the decision function, the greater the reactivity.

The above automatic scoring system of the invention may be used to extend the commonly used observational scoring systems to cover deep sedation levels, i.e. patients that no more have observable responses.

In the above embodiments, the measurement is generally indicative of the reactivity of the central nervous system of a patient to external stimulation. However, if desired, the measurement may also be made specific to the cortical state only. In such an embodiment, magnetic stimulation of the cortex may be employed to avoid a situation in which damaged neural pathways within the sensory nervous system or between the sensory nervous system and the cortex may obscure the real cortical state of the patient. In transcranial magnetic stimulation (TMS) the cerebral cortex can be stimulated without health risks and pain by applying a strong magnetic field with the help of at least one coil placed on the head. The magnetic field induces an electric current at a desired point. The induced current activates a group of cortical neurons. Hence, direct magnetic stimulation of the cortex can be used as a stimulus when testing the EEG reactivity. Furthermore, TMS provides an efficient tool for assessing deep levels of sedation or unconsciousness, since TMS stimulation may be relatively stronger stimuli than the stimuli sensed through the sensory nervous system.

Thus, in an embodiment employing magnetic stimulation, the stimulating system comprises at least one coil and a current source connected to the coil(s). The current source is configured to supply a current pulse to the coil(s), which may be placed by the nursing staff on or above the vertex of the head of the patient to stimulate the patient's cortex directly. Since magnetic stimulation of the cortex is known as such, the stimulating system is not discussed in detail in this context. The stimulating system may be similar to the one disclosed in U.S. Pat. No. 6,256,531, for example, which discloses a method and apparatus for mapping cortical connections.

Since the stimulus is in this embodiment not supplied through the sensory nervous system of the subject, the state of the sensory nervous system cannot affect the measurement, but the measurement is specific to the cortical state only.

The above embodiments may also be combined so that a measurement employing at least one stimulus sensed through the sensory nervous system is performed first. Depending on the situation, a further measurement employing magnetic stimulation of the cortex may be performed after the first measurement. The further measurement may be performed, for example, if the first measurement indicates lack of reactivity or low reactivity, thereby to test the state of the sensory nervous system. Altenatively, the further measurement may be performed regardless of the result of the first measurement, to verify the result of the first measurement.

Because the detection of EEG reactivity is sometimes difficult even for an experienced human observer, the same stimulus may be supplied twice in a row with a certain inter-stimulus-interval, such as 30 seconds. Parallel comparison of EEG waveforms before and after both stimuli facilitates decision-making. This kind of comparison may be carried out with the technique of this invention. For example, in the first step prior-stimulus autocorrelation functions are compared with each other, as well as are the post-stimulus autocorrelation functions. If the comparison of the first step indicates that the EEG contains similar characteristics, i.e. if autocorrelation functions are relatively similar, the second step compares autocorrelation functions before and after both stimuli. If this comparison indicates changes after both stimuli, reactivity is detected.

Figure 8A:
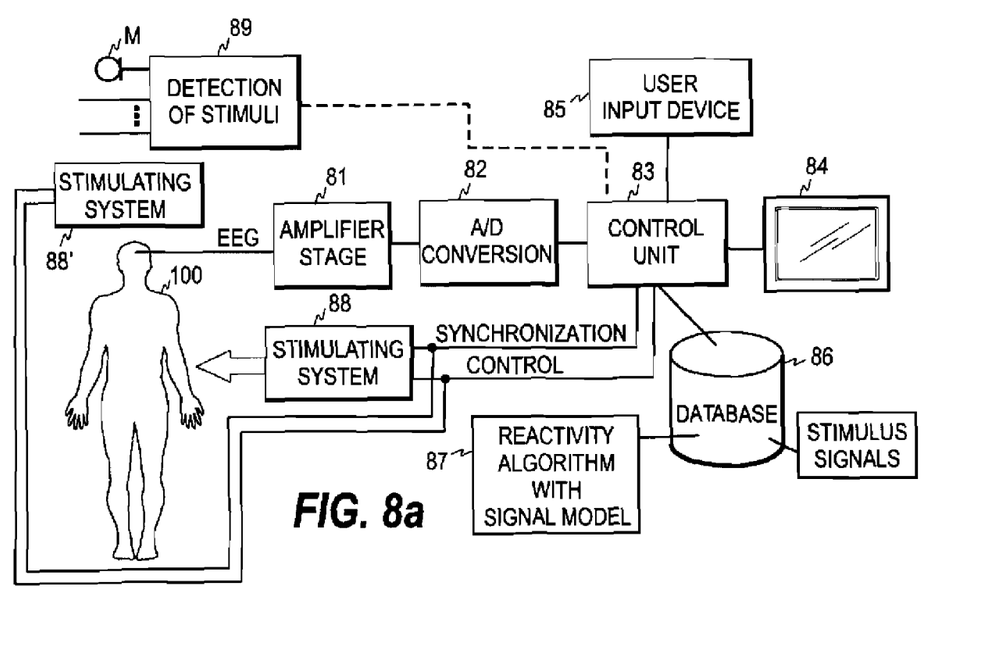
FIG. 8a illustrates one embodiment of the apparatus/system of the invention.

FIG. 8a illustrates one embodiment of the system or apparatus according to the invention. The EEG signal data obtained from electrodes applied to the forehead of a patient 100 is supplied to an amplifier stage 81, which amplifies the signal(s) before they are sampled and converted into digitized format in an A/D converter 82. The digitized signals are supplied to a control unit 83 which may comprise one or more computer units or processors.

Figure 8B:
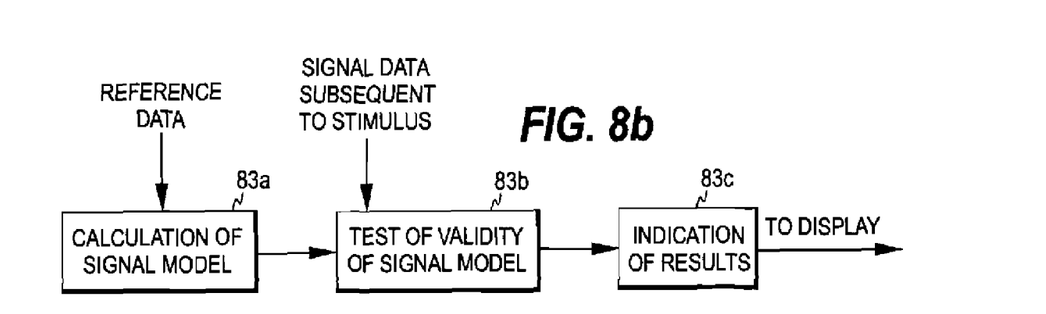

The computer unit is provided with a memory or database 86 holding the digitized signal data obtained from the electrodes. The memory or database may also store one of the EEG reactivity algorithms 87 described above. The reactivity algorithm includes the signal model or data necessary to construct the model. The control unit executes the stored algorithm, whereby an indication or a measure of EEG reactivity is obtained as disclosed in connection with FIGS. 1, 2, 6, and 7. Various data needed by the algorithm, such as the reactivity values that correspond to the stimuli, may be pre-stored in the memory or the algorithm may calculate such data. As shown in FIG. 8b, the control unit may thus include three successive operational modules or units: a calculation module 83a for constructing, based on a segment of time series of a physiological signal obtained from a subject, a signal model for the physiological signal, a test module 83b for testing, based on further signal data obtained from the subject, whether the signal model is a valid signal model for the physiological signal, and an indication module 83c for indicating to the user whether reactivity is present in the physiological signal. The indication module may be drive a display device 84 to display the reactivity indicator, its trend, and the above-described user notifications on the screen of the display, which thus forms part of the user interface of the device. As obvious from above, the reactivity indicator displayed may simply be on/off information indicating whether reactivity is present or not. However, it is also possible that the system only displays information from which the user may not directly see, but may deduce, whether or not reactivity is present, such as the prediction error and the associated threshold.

Although a control unit comprising one computer unit or one processor may perform the above steps, the processing of the data may also be distributed among different units/processors (servers) within a network, such as a hospital LAN (local area network). The apparatus of the invention may thus also be implemented as a distributed system.

The monitoring device may further be provided with one or more stimulator units 88, 88' for giving the stimuli. As discussed above, the stimulus generated by the stimulator unit may assume many forms and the stimulus signals may be aligned with the EEG signal in various ways. The characteristics of the available stimuli may be stored in the memory 86 of the system/apparatus. The system may comprise one unit 88 for generating stimuli sensed through the sensory nervous system and another unit 88' for generating electromagnetic stimulus pulses. Preferably, all the stimulators form an integrated whole with the EEG device being either integrated parts of it or plug-in modules.

The user may control the operation of the monitoring device through a user input device 85, such as a keyboard. The computer or control unit 83 controls the stimulator unit according to the commands given by the user from the user input device.

In the above embodiments, the stimulus/stimuli is/are produced intentionally to assess the EEG reactivity. However, the apparatus of the invention may also monitor the clinical environment to detect the natural stimuli occurring therein. The natural stimuli may be originated from various sources, and one or more such sources may be monitored by a monitoring unit 89 shown in FIG. 8. For example, the noise level may be recorded through a microphone M, and presence of EEG reactivity may be determined when a noise peak of sufficient amplitude is detected. Thus, in this embodiment no stimulation unit is needed but the natural stimuli occurring in the environment are monitored. Since the occurrence of the noise peak cannot be anticipated, the signal model is continuously updated based on the latest EEG signal data obtained from the patient.

A conventional patient monitor intended for measuring the level of consciousness may also be upgraded to enable the monitor to detect the EEG reactivity of a patient.

Such an upgrade may be implemented by delivering to the monitoring device a plug-in software module that enables the device to evaluate reactivity based on the time series of the EEG signal data stored in the device. The software module may be delivered, for example, on a data carrier, such as a CD or a memory card. The software-based upgrade may be such that it supports the manual stimulus indication given by the user through a user input device of the patient monitor, in which case no stimulus unit is needed in the monitor.

Figure 9:
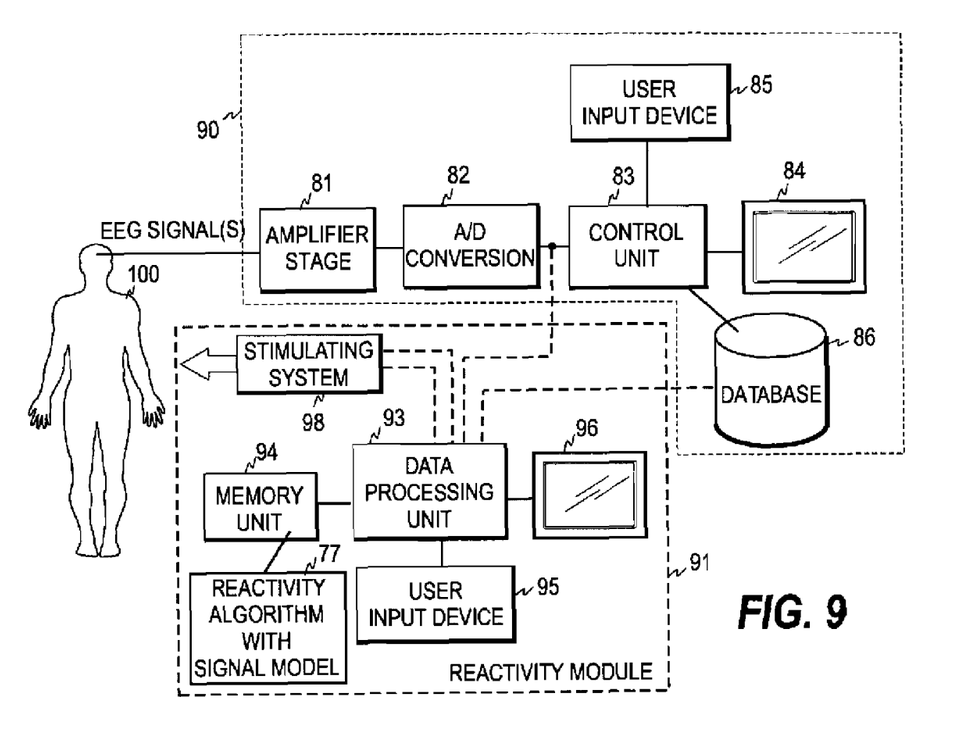
FIG. 9 illustrates another embodiment of the apparatus/system of the invention.

The upgrade may also be implemented as a separate reactivity module connectable to a conventional patient monitor intended for measuring the level of consciousness. As is shown in FIG. 9, such a module 91 may comprise a data processing unit 93 which receives the time series of the EEG signal data from a conventional patient monitor 90 and detects or derives the EEG reactivity from the said data. The data processing unit 93 is provided with a memory unit 94 holding the digitized signal data obtained from the patient monitor 90. The memory unit 94 may also store one of the EEG reactivity algorithms 77 described above.

The reactivity module 91 may optionally include the above-described stimulator unit 98, especially if the conventional monitor to which the module is connectable is not provided with such a unit. However, as is obvious from the above, a stimulator unit is not necessarily needed in the reactivity module even if the conventional monitor failed to have any stimulation unit. Namely, the user may give the stimulus signal manually, using a horn, for example, and indicate the moment of the stimulus signal through the user input device 95 of the module. The user may, for example, press a certain button simultaneously when he/she gives the stimulus signal. The reactivity module may further comprise a display 96 of its own for displaying the reactivity indicators to the user.

Above, the invention was employed for assessing the EEG reactivity of a patient. However, depending whether a test of the reactivity of another physiological signal than the EEG provides valuable information about the patient, the same mechanism may be used in connection with said another physiological signal. Therefore, the invention is not necessarily limited to the context of EEG.

Although the invention was described above with reference to the examples shown in the appended drawings, it is obvious that the invention is not limited to these, but may be modified by those skilled in the art without departing from the spirit and scope of the invention. For example, the time reference applied is not necessarily the time instant of the stimulus, if the reactivity appears only after a certain delay.

The invention claimed is:

1. An apparatus for assessing physiological signal reactivity of a subject, the apparatus comprising:
   a first reception unit configured to receive a single continuous physiological signal from the subject;
   a calculation unit configured to construct, based only on a time series of a physiological signal obtained from the subject, a signal model for the physiological signal;
   a control unit configured to apply a single time reference to the time series corresponding to a stimulus supplied to the subject;

a second reception unit configured to receive further signal data from the time series of the physiological signal, the further signal data being obtained from the subject subsequent to the time reference;

a test unit configured to test, through employment of the signal model constructed from the physiological signal obtained at least partially prior to the single time reference and the further signal data obtained subsequent to the single time reference whether the signal model is a valid signal model for the physiological signal; and an indicator unit, responsive to the test unit, configured to indicate, whether reactivity is present in the physiological signal.

2. An apparatus according to claim 1, wherein the physiological signal is an EEG signal.

3. An apparatus according to claim 1, further comprising a stimulation unit configured to supply the stimulus to the subject.

4. An apparatus according to claim 3, wherein the stimulus is a selected stimulus in a sequence comprising a plurality of stimuli in ascending order of intensity.

5. An apparatus according to claim 3, wherein the stimulation unit is further configured to induce an electromagnetic pulse in the interior of the subject's head.

6. An apparatus according to claim 1, wherein the calculation unit is configured to construct an autoregressive model.

7. An apparatus according to claim 1, wherein the test unit is configured to
calculate a prediction value based on the signal model and
define a prediction error based on the further signal data and the prediction value.

8. An apparatus according to claim 7, wherein the test unit is configured to compare the prediction error with a predetermined threshold value.

9. An apparatus according to claim 7, wherein the prediction error is dependent on the difference between the prediction value and a value obtained in the further signal data.

10. An apparatus according to claim 1, wherein
the calculation unit is configured to derive the signal model based on a first time window of the time series and first data based on the signal model, and
the test unit is configured to define (i) a further signal model based on a second time window of the time series and second data based on the further signal model, wherein the second time window includes the further signal data, and (ii) an error value dependent on the difference of the first and second data.

11. An apparatus according to claim 10, wherein the signal model and the further signal model are dependent on an autocorrelation function.

12. An apparatus for assessing physiological signal reactivity of a subject in a single trial analysis, the apparatus comprising:
a first reception means for receiving a single continuous physiological signal from the subject;
calculation means for constructing, based only on a time series of a physiological signal obtained from the subject, a signal model for the physiological signal;
control means for applying a single time reference to the time series corresponding to the time a stimulus is supplied;
a second reception means for receiving further signal data from the time series of the physiological signal, the further signal data being obtained from the subject subsequent to the time reference;
testing means for testing, through employment of the signal model constructed from the physiological signal obtained at least partially prior to the single time reference and further signal data obtained subsequent to the single time reference, whether the signal model is a valid signal model for the physiological signal; and
indicator means, responsive to the test unit, for indicating, whether reactivity is present in the physiological signal.

13. A computer program product embodied on a non-transitory computer-readable medium for assessing physiological signal reactivity of a subject, the computer program product comprising:
a first program code portion configured to construct, based on a time series of a physiological signal obtained from the subject, a valid signal model for the physiological signal;
a second program code portion configured to apply a single time reference to the time series corresponding to when a stimulus is supplied;
a third program code portion configured to test, through employment of the signal model constructed from the physiological signal obtained at least partially prior to the single time reference and further signal data of the time series of the physiological signal, whether the signal model is a valid signal model for the physiological signal, wherein the further signal data is subsequent to the time reference; and
a fourth program code portion, responsive to the third program code portion, configured to indicate whether reactivity is present in the physiological signal.

* * * * *